US009250061B2

(12) United States Patent
Lorbeer et al.

(10) Patent No.: US 9,250,061 B2
(45) Date of Patent: Feb. 2, 2016

(54) TECHNIQUE FOR TOMOGRAPHIC IMAGE RECORDING

(75) Inventors: Raoul-Amadeus Lorbeer, Hannover (DE); Heiko Meyer, Isernhagen (DE); Marko Heidrich, Hannover (DE); Alexander Heisterkamp, Isernhagen (DE)

(73) Assignee: LASER ZENTRUM HANNOVER E.V., Hannover (DE)

( * ) Notice: Subject to any disclaimer, the term of this patent is extended or adjusted under 35 U.S.C. 154(b) by 170 days.

(21) Appl. No.: 13/994,589

(22) PCT Filed: Dec. 16, 2011

(86) PCT No.: PCT/EP2011/073077
§ 371 (c)(1),
(2), (4) Date: Dec. 12, 2013

(87) PCT Pub. No.: WO2012/080478
PCT Pub. Date: Jun. 21, 2012

(65) Prior Publication Data
US 2014/0085623 A1 Mar. 27, 2014

(30) Foreign Application Priority Data
Dec. 17, 2010 (DE) .......................... 10 2010 063 412

(51) Int. Cl.
*G01N 21/00* (2006.01)
*G01B 9/02* (2006.01)
(Continued)

(52) U.S. Cl.
CPC ........ *G01B 9/02091* (2013.01); *G01N 21/4795* (2013.01); *G01N 21/6408* (2013.01); *G01N 21/6458* (2013.01); *G01N 2021/1787* (2013.01); *G01N 2201/065* (2013.01)

(58) Field of Classification Search
CPC ............. G01B 9/0291; G01N 21/4795; G01N 2021/1787
See application file for complete search history.

(56) References Cited

U.S. PATENT DOCUMENTS 4,022,529 A * 5/1977 White ........................... 356/318
6,646,742 B1 11/2003 Gangstead et al.
(Continued)

FOREIGN PATENT DOCUMENTS

DE 4326473 A1 2/1995
EP 1520173 B1 2/2006
(Continued)

OTHER PUBLICATIONS

International Search Report Issued in PCT Application No. PCT/EP2011/073077, dated May 2, 2012.
(Continued)

*Primary Examiner* — Gregory J Toatley
*Assistant Examiner* — Shawn Decenzo
(74) *Attorney, Agent, or Firm* — The Marbury Law Group PLLC

(57) ABSTRACT

The invention relates to a device (10; 210; 310; 410; 510) for tomographic image recording. The device comprises a sample retainer (14), a light source (12), and a detector unit (16). The light source (12) is designed to produce a pencil beam (38), which has a beam direction (40) and which passes through a sample volume of the sample retainer (14) provided in order to accommodate a sample, and has an optical control element (30), which is able to move the pencil beam (38) passing through the sample retainer (14) transversely to the beam direction (40) while the beam direction (40) remains substantially unchanged. The detector unit (16) is designed to detect at least a portion of scattered radiation (64; 64') escaping from a section of the pencil beam (38) within the sample volume or the sample retainer (14) in a non-spatially-resolved manner.

25 Claims, 7 Drawing Sheets

(51) Int. Cl.
*G01N 21/47* (2006.01)
*G01N 21/64* (2006.01)
*G01N 21/17* (2006.01)

(56) References Cited

U.S. PATENT DOCUMENTS

| | | | |
|---|---|---|---|
| 7,633,048 B2 | 12/2009 | Doran et al. | |
| 2007/0109633 A1 | 5/2007 | Stelzer | |
| 2007/0274580 A1 | 11/2007 | Ntziachristos et al. | |
| 2008/0226025 A1* | 9/2008 | Harding et al. | 378/44 |
| 2008/0277567 A1 | 11/2008 | Doran et al. | |
| 2010/0078576 A1* | 4/2010 | Ntziachristos et al. | 250/459.1 |
| 2012/0230918 A1* | 9/2012 | Dobosz et al. | 424/9.6 |

FOREIGN PATENT DOCUMENTS

| | | |
|---|---|---|
| EP | 1530073 B1 | 11/2007 |
| JP | 2007528500 A | 10/2007 |
| JP | 2009545737 A | 12/2009 |
| WO | 2004020997 A1 | 3/2004 |
| WO | WO2009/133734 A1 | 11/2009 |

OTHER PUBLICATIONS

Lorbeer et al., "Highly Efficient 3D Fluorescence Microscopy with a Scanning Laser Optical Tomograph," Optics Express, vol. 19, No. 6, 14, Mar. 14, 2011.

Heidrich et al., "3D Imaging of Biofilms on Implants by Detection of Scattered Light with a Scanning Laser Optical Tomograph," Biomedical Optics Express, vol. 2, No. 11, Nov. 1, 2011.

Sharpe et al., "Optical Projection Tomography as a Tool for 3D Microscopy and Gene Expression Studies," Science 296, 541 (2002).

Meyer, "A Multiprojection Noncontact Fluorescence Tomography Setup for Imaging Arbitrary Geometries," Proceedings of SPIE, vol. 5693, Jan. 2005.

Takeda et al., "Biomedical Imaging by Fluorescent X-Ray Micro-Computed Tomography," Proc. JSBB 1B-5, pp. 112-117, 2001.

Takeda et al., "Medical Imaging by Fluorescent X-Ray CT: Its Preliminary Clinical Evaluation," SIPE Proceeding Paper, Jan. 7, 2002, DOI: 101117/12.452856.

Razansky et al., "Multispectral Opto-Acoustic Tomography of Deep-Seated Fluorescent Proteins in Vivo," Nature Photonics, vol. 3, Jul. 2009.

Krstajic et al., "Initial Characterization of Fast Laser Scanning Optical CT Apparatus for 3-D Dosimetry," J. Phys.: Conf. Ser. 164 (2009).

Walls et al., "Correction of Artefacts in Optical Projection Tomography," Phys. Med. Biol. 50 (2005).

Meyer et al., "Optical Projection Tomography for In-Vivo Imaging of Drosophila Melanogaster," Microscopy and Analysis 22(5): 19-22 (EU), 2008.

Pogue et al., "Forward and Inverse Calculations for 3D Frequency-Domain Diffuse Optical Tomography," Proc. SPIE 2389, Optical Tomography, Photon Migration, and Spectroscopy of Tissue and Model Media: Theory, Human Studies, and Instrumentation, 328 (May 30, 1995).

Japanese Office Action Notification of Reasons for Refusal for Japanese Patent Application No. 2013-543819, dated Nov. 4, 2015, (8 pages).

* cited by examiner

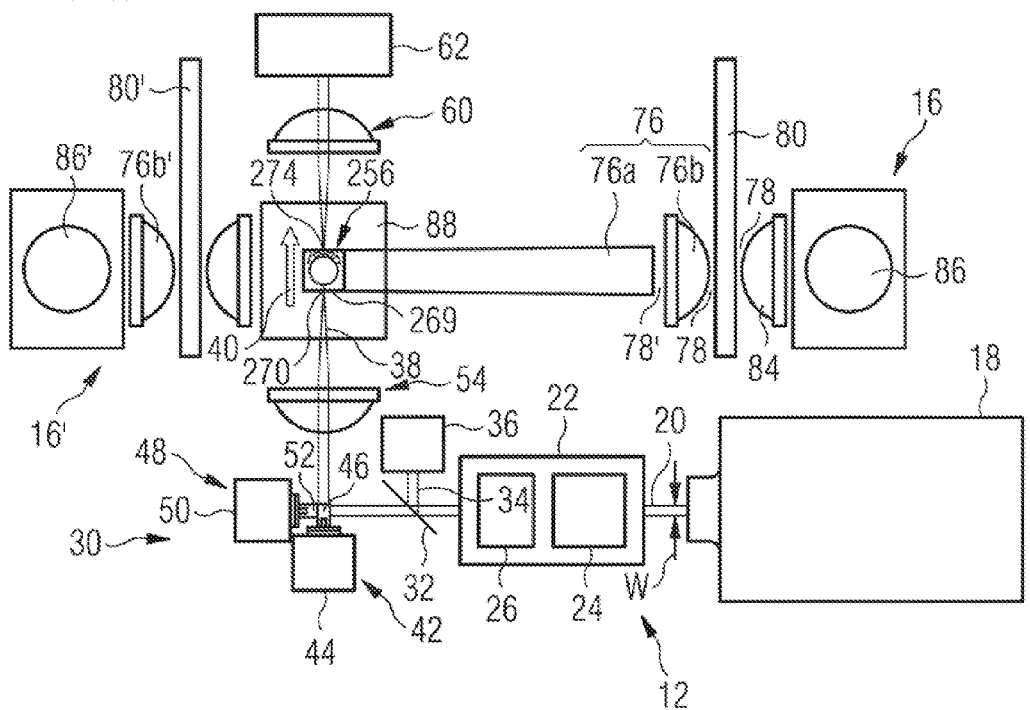

TECHNIQUE FOR TOMOGRAPHIC IMAGE RECORDING

CROSS-REFERENCE TO RELATED APPLICATIONS

This application is a National Stage application of PCT International Application Serial No. PCT/EP2011/073077, filed Dec. 16, 2011, which claims priority from German Application No. 10 2010 063 412.3, filed Dec. 17, 2010.

TECHNICAL FIELD

The invention relates generally to a technique for acquiring a sectional image or a three-dimensional image. In particular, the invention relates to an apparatus for tomographic acquisition of an image of a spatial object.

TECHNICAL BACKGROUND

Resolution and contrast of existing techniques for spatial image acquisition, particularly for microscopy of living organisms, have been significantly improved in recent years. Widespread techniques with high resolution, such as the confocal microscopy described in printed publication DE 43 26 473, are based on the spatially resolved acquisition of an overlap of illumination volume and acquisition volume. The volume of the overlap determines the resolution. Alternative processes, such as optical coherence microscopy (OCM) and optical coherence tomography (OCT), determine the axial depth interferometrically by means of light of short coherence length. More recent techniques, such as the optical projection tomography (OPT) described in Science 296, 541 (2002) by J. Sharpe et al., transirradiate the specimen volume at a plurality of different angles and attain a dependent resolution from 1 μm to 5 μm.

Document WO 2004/020997 A1 describes an apparatus with a rotatable object stage for rotating the specimen to be imaged. A main detector acquires only light that leaves the specimen parallel to the light-incidence direction. In further embodiments, a main detector and a plurality of auxiliary detectors have been arranged in a one-dimensional or two-dimensional matrix in the beam direction downstream of the specimen with a view to angle-resolved acquisition of light, whereby light deflected from the specimen is acquired by the auxiliary detectors.

Document US 2007/0109633 A1 describes a microscope that transilluminates a plane in the specimen volume with a set of parallel beams of light. The illumination plane that is formed in this manner is acquired in its two dimensions by a CCD camera at a right angle to the illumination plane in spatially resolved manner. In a further embodiment, two illumination planes are irradiated. By superimposition of two coherent illumination planes, the intensity distribution in the superimposed illumination plane is structured by interference patterns with a view to improving the positional resolution in the illumination plane. With a view to spatial image acquisition, the illumination plane and the specimen are moved towards one another. A further embodiment illuminates the specimen substantially one-dimensionally and acquires the specimen in this dimension in spatially resolved manner with a linearly increased number of pixels.

Document US 2007/0274580 A1 describes a technique for optical tomography. Fluorescent proteins in a specimen are excited by incident light. The exciting light in the specimen and the fluorescent light are diffuse. A spatially resolved image is acquired and processed.

The science publication "Forward and Inverse Calculations for 3-D Frequency-Domain Diffuse Optical Tomography", B. W. Pogue et al., SPIE Vol. 2389, pages 328-339, describes a process of diffusive optical tomography (DOT). For a simulation of the process it is assumed that a plurality of detectors have been arranged around an object on a circle.

The known techniques for spatial image acquisition can, by reason of a radiation intensity acting on the specimen, distort the image acquisition, change the specimen in uncontrolled manner or, particularly in the case of in vivo microscopy, destroy the specimen. Also, the technical effort in order with the prior techniques to diminish the radiation intensity with comparable image results may rise considerably.

SUMMARY

The object underlying the invention is to make available an improved apparatus for tomographic image acquisition.

The object is achieved by an apparatus for tomographic image acquisition having the features of Claim 1.

An apparatus for tomographic image acquisition may include:
 a specimen holder,
 a light-source which has been designed for generating a pencil beam with a beam direction traversing the specimen holder, and which exhibits an optical control element which is able to offset the pencil beam traversing the specimen holder at right angles to the beam direction, with substantially unchanged beam direction, and
 a detector unit which has been designed for non-spatially-resolved acquisition of at least a portion of a scattered radiation escaping from a section of the pencil beam within the specimen holder.

The specimen holder may provide a specimen volume for receiving a specimen. The pencil beam may traverse the specimen holder, the specimen volume and/or the specimen.

The apparatus can acquire the scattered radiation escaping by reason of an individual pencil beam (at right angles to the beam direction). In comparison with conventional techniques, in this way a considerably larger proportion of the scattered radiation is capable of being acquired by the detector unit. Accordingly, the signal-to-noise ratio of the acquisition can be significantly improved. Also, a radiation intensity (with identical or improved image quality) introduced by the pencil beam can be diminished. In addition, a signal mixing of pencil beams that have been offset (parallel) relative to one another (i.e. various measuring positions) can be excluded. Also, the specimen volume can be acquired with a uniform sensitivity, insofar as the same detector unit acquires all the measuring positions. In particular, ring artefacts (such as frequently arise in the course of the tomographic reconstruction of a spatially resolved acquisition) can be avoided. In comparison with the spatially resolved acquisition of conventional techniques, the acquisition by the detector unit may be regarded as "zero-dimensional". Furthermore, a more homogenous (in effect) illumination of the specimen volume, in particular at right angles to the beam direction, in comparison with a simultaneous illumination (which, for instance, employs a diffuser) can be obtained. Advantageously, for an excitation of the scattered radiation that is as homogeneous as possible the light-source comprises a laser that is stable (over an image acquisition time) by way of radiation-source.

Generally, the radiation-source may be substantially spatially coherent, in particular punctiform. A preferred radiation-source is a laser. For example, the radiation-source may be a source of fluorescent light, preferentially a superluminescent diode (SLD) with a small exit aperture. A diameter of the exit aperture may have been defined to be so small that the exit aperture is at least substantially diffraction-limited. Preferentially, the diameter of the exit aperture corresponds (at most) to twice the diffraction limitation.

"Scattered radiation" encompasses any radiation brought about by (electromagnetic, quantum-physical or thermal) interaction of the pencil beam with a specimen received in the specimen holder (in particular with the pigments, scattering centres, molecules or atoms thereof). In particular, the term "scattered radiation" encompasses radiation brought about by fluorescence, Raman scattering, Rayleigh scattering and Mie scattering. Furthermore, the scattered radiation may have been defined by a scattering direction deviating from the beam direction of the pencil beam, by a scattered-radiation characteristic (according to a differential scattering cross-section) or by a wavelength different from the pencil beam.

"Scattered radiation escaping" from the pencil beam may (exclusively) encompass scattered radiation scattered out of the beam direction. In the case of fluorescent radiation, scattered radiation in the beam direction can also be acquired by means of a dichroic filter.

In the case of fluorescent radiation by way of scattered radiation, "non-resonant fluorescence" encompasses the case of a fluorescence wavelength (of the fluorescent radiation emitted as scattered radiation) that is longer than the excitation wavelength (of the pencil beam radiated in for the purpose of excitation).

The non-spatially-resolved acquisition may be non-spatially-resolved in the beam direction. The non-spatially-resolved acquisition may furthermore be non-directionally resolved. Preferentially, the non-directionally-resolved acquisition is non-directionally resolved with respect to a specimen exit direction.

The specimen holder may be transparent to the beam at least in one section (also designated as a "window") of the specimen holder.

The image acquisition can be repeated (by rotation about the axis of rotation) in various rotary positions (i.e. various directions of incidence) of the pencil beam (relative to the specimen holder). Given lesser complexity (of a specimen object to be represented), a number of the various different rotary positions may be smaller. In this way, in the case of a two-dimensional (at most) specimen object two different rotary positions can be acquired (and a specimen image can be reconstructed by triangulation). The axis of rotation may pass through the specimen holder. This includes the case where only an imaginary rectilinear extension of a structural axis of rotation passes through the specimen holder.

The light-source may be stationary, and the specimen holder may be rotatable about the axis of rotation. Alternatively, the specimen holder may be stationary and the light-source may be rotatable about the axis of rotation.

The pencil beam may exhibit a defined beam width within the specimen holder. The pencil beam may be substantially free from divergence within the specimen holder. The pencil beam may exhibit a beam waist within the specimen holder having a Rayleigh length that is substantially equal to or greater than (half) the length of the acquired section.

The length of the acquired section may be greater than the beam width by a multiple. The beam width may be smaller by a multiple than one or all of the internal dimensions of the specimen holder at right angles to the beam direction. The acquired section may comprise the entire pencil beam traversing the specimen holder.

The light-source may furthermore have been designed to generate the pencil beam in the visible spectrum, in the ultraviolet spectrum, or in the infrared spectrum. Generally, the pencil beam may lie within the electromagnetic spectrum having (vacuum) wavelengths from 300 nm to 2000 nm. This spectrum is suitable for non-destructive acquisition of an image of a specimen of deoxyribonucleic acid (DNA). A preferred spectral range of the pencil beam encompasses 323 nm to 750 nm or 355 nm to 850 nm (in the case of fluorescent radiation by way of scattered radiation). In conjunction with absorption tomography (by means of a transmission photodetector), the pencil beam may (additionally) exhibit radiation from 200 nm to 323 nm (or from 200 nm to 355 nm). Furthermore, the pencil beam may excite the scattered radiation at least partly in the extreme-ultraviolet spectrum (XUV) or in the far-infrared spectrum (FIR). In the case of a water-free specimen, the pencil beam may (additionally) exhibit radiation within the range above 2000 nm. With a view to multi-photon excitation of the fluorescent radiation (in short: "multi-photon fluorescence"), each wavelength specification above (of a spectral range boundary) can be multiplied by a factor of 2 (in the case of a two-photon excitation), by a factor of 3 (in the case of a three-photon excitation), etc. With a view to multi-photon excitation, the light-source may emit brief intense pulses. A femtosecond laser or a (Q-switched) laser with pulse durations of a few picoseconds can be employed as radiation-source for multi-photon excitation. The multi-photon fluorescence can enable the acquisition of a greater depth (in the beam direction).

Alternatively or in supplement, the light-source may have been designed to generate, by means of the pencil beam, second harmonics (i.e. frequency doubling), or high harmonics, which are designated here comprehensively as "higher harmonics", in the specimen holder (i.e. in the specimen employed in the given case). This process (mostly designated in the technical terminology as higher-harmonic generation or HHG) can coherently transform several (two, three or more) photons (of the pencil beam) into one photon. The "scattered radiation" resulting therefrom may exhibit a higher frequency, (by approximation) higher by an integral multiple, (and correspondingly shorter wavelength) than the pencil beam. The direction of the "scattered radiation" of the HHG may, in principle, be in the beam direction (of the pencil beam) or opposite to the beam direction. The "scattered radiation" of the HHG is capable of being generated along the section of the pencil beam within the specimen holder (and not only at a focal point). HHG may also occur without addition of so-called "markers" (to the specimen). Preferentially, for the HHG the light-source for generating the pencil beam has been designed with circular polarisation. The "scattered radiation" of the HHG may furthermore generate (secondary) scattered radiation at scattering centres within the specimen holder (i.e. in the specimen employed in the given case). Advantageously, by virtue of the circularly polarised pencil beam the (secondary) scattered radiation is capable of being generated at scattering centres independently of a spatial orientation of the scattering centres.

The detector unit includes at least one scattered-radiation collector which has been designed, or which have together been designed, to acquire the scattered radiation within a solid angle about the specimen holder of at least $0.12\,\pi$ sr (or at least $\pi/8$ sr), as an example about $0.4\,\pi$ sr, and preferentially at least $2\pi$ sr. The acquired solid angle of $0.12\,\pi$ sr may correspond to a (maximal) photon efficiency of 3%. Furthermore, the acquired solid angle of $0.12\,\pi$ sr may correspond to a numerical aperture of about NA=0.5 (using an immersion liquid). In air, a numerical aperture of NA=0.5 may correspond to an acquired solid angle of $0.28\,\pi$ sr (or a maximal photon efficiency of 7%). The scattered radiation acquired in this way within the solid angle may be acquired coherently or incoherently. Advantageously it is (possible but) not necessary to acquire the scattered radiation coherently. In particular, radiation paths of the acquired scattered radiation may also exhibit differing optical path lengths, which differ by more than one coherence length.

The detector unit may furthermore include as a signal generator a semiconductor detector and/or a photomultiplier tube (PMT). The semiconductor detector may be a phototransistor or a photodiode, preferentially an avalanche photodiode (APD).

The specimen holder may have been designed to receive a liquid (viscous) specimen environment. The specimen holder and/or a liquid (viscous) specimen environment within the specimen holder may exhibit a refractive index adapted to the specimen.

A first collimator of the scattered-radiation collector may include a strongly refracting lens or a condenser lens which has been designed to collimate the acquired scattered radiation. Alternatively or additionally, the scattered-radiation collector may exhibit as first collimator a tapered light guide (tapered light pipe, TLP) which has been designed to collimate the acquired scattered radiation. The light guide may be a reflection-coated (on the inside) optical hollow-core conductor. Alternatively, the light guide may be a solid glass rod, so that the scattered radiation is guided by total reflection (for instance, to the air surrounding the solid glass rod). Alternatively or in supplement, the solid glass rod may have been vapour-coated with a dichroic layer. The dichroic layer can reflect the scattered radiation for steep angles of incidence (i.e. small angles of incidence relative to the normal to the inner surface of the optical hollow-core conductor). This can enable reflection (on the dichroic layer) to occur for steep angles, and total reflection to occur for shallow angles (i.e. for large angles of incidence with the normal to the inner surface of the optical hollow-core conductor).

The detector unit may furthermore exhibit one or more exchangeable fluorescence filters which are substantially transparent to fluorescent radiation (by way of scattered radiation). The fluorescence filter(s) may be substantially opaque within the bandwidth of the pencil beam. The fluorescence filter may be a colour filter or a dichroic filter.

The filter-option unit may include the several exchangeable fluorescence filters. The filter-option unit may have been designed to arrange the fluorescence filters optionally (individually) between the first collimator and the signal generator. In this way, the filter-option unit may include a rotatable wheel disc in which the several fluorescence filters have been set circumferentially. The exchangeable fluorescence filter may be capable of being chosen by the rotation. Alternatively, the filter-option unit may be a displaceable slide, along which the several fluorescence filters have been set. The exchangeable fluorescence filter may be capable of being chosen by the displacement.

The detector unit may exhibit a second collimator which has been arranged between the fluorescence filter and the signal generator for the purpose of focusing the acquired scattered radiation.

The detector unit may include several scattered-radiation collectors. The detector unit may furthermore include a signal generator assigned to all the scattered-radiation collectors, or several signal generators each assigned to one of the scattered-radiation collectors. Signal outputs of the several signal generators can be added up. The signal outputs can be added up in analogue manner, preferentially by the signal outputs having been interconnected. Alternatively or in supplement, the signal outputs can be added up digitally, preferentially by an analogue-to-digital converter having been connected to or being capable of being connected to each of the signal outputs for the purpose of separate digitisation, and by a computing unit having been connected to or being capable of being connected to the analogue-to-digital converter for the purpose of addition of the digitised signal outputs.

The scattered-radiation collector may furthermore exhibit an integrator at least substantially surrounding the specimen holder. An inner surface (facing towards the specimen holder) of the integrator may be a diffusely reflecting inner surface. The inner surface of the integrator may exhibit a cuboid shape. Alternatively, the integrator may be an Ulbricht sphere. A linear dimension of the integrator, preferentially an edge length or a diameter of the integrator, may be so small that a light propagation time corresponding to the linear dimension is shorter than a half-life of the fluorescent radiation excited by the pencil beam. In this connection, the linear dimension may furthermore have been multiplied by an (average) number of reflection events or scattering events (within the integrator). The half-life of the fluorescent radiation (i.e. a fluorescence lifetime) may in this way be capable of being acquired, particularly if the temporal broadening (of a signal) of the scattered radiation by virtue of variably long light propagation distances is small in comparison to the half-life. The first collimator may for this purpose have been arranged to receive scattered radiation at a measuring aperture in the integrator arranged substantially perpendicular to the beam direction.

The optical control element of the light-source may include:
  at least one rasterisation mirror, and
  one or more actuators coupled with the at least one rasterisation mirror, for moving the rasterisation mirror.

In particular, the optical control element may have been designed as a relay lens system with:
  a first rasterisation mirror actuated by a first actuator for offsetting the pencil beam in a first rasterisation direction,
  a second rasterisation mirror actuated by a second actuator for offsetting the pencil beam in a second rasterisation direction substantially perpendicular to the first rasterisation direction, and
  a lens, two lenses or a lens system (between the first rasterisation mirror and the second rasterisation mirror) which has/have been designed to image the first rasterisation mirror onto the second rasterisation mirror.

The optical control element may be voltage-controlled, preferentially capable of being actuated piezoelectrically. In this way, a piezoelectric crystal may have been employed as actuator. Alternatively, the optical control element may be current-controlled, preferentially by means of a moving-magnet galvanometric drive or a moving-coil galvanometric drive. In this way, a galvanometric drive (also designated as galvo-scanner) may have been employed as actuator. Alternatively, the optical control element (for each of the two rasterisation directions) may exhibit a polygon scanner. The polygon scanner includes a mirror polygon and a motor, on the axis of which the mirror polygon has been rotatably arranged. The mirror polygon is a cylinder with a regular polygon as base, the lateral faces of which are silvered. Furthermore, the optical control element (for each of the two rasterisation directions or for a fast-rasterisation direction) may exhibit an acousto-optic modulator (AOM). As optical control element, the AOM is also designated as acousto-optic deflector (AOD). The AOM includes a beam-transparent solid body in which a piezoelectric element arranged at right angles to the beam direction is able to generate an ongoing soundwave having an ultrasonic frequency. With a view to fast rasterisation (i.e. for offsetting the pencil beam), the ultrasonic frequency is variable.

The one or more actuators may have been designed to move the rasterisation mirror substantially perpendicular to the beam direction, or to swivel it about a swivel axis substantially perpendicular to the beam direction. For the purpose of offsetting the pencil beam in a first rasterisation direction and in a second rasterisation direction that is not parallel to the first rasterisation direction, a first actuator and a second actuator of the several actuators may have been provided. The first rasterisation direction is preferentially (substantially) parallel to the axis of rotation.

The light-source may furthermore exhibit a radiation-source and a beam-shaping lens system which has been arranged between the radiation-source and the optical control element. The beam-shaping lens system may include a telescopic lens system for beam enlargement. Furthermore, the beam-shaping lens system may include an annular diaphragm and an axicon for generating a Bessel beam by way of pencil beam. Alternatively or in supplement, the beam-shaping lens system may include a spiral phase plate (vortex phase plate) for generating the pencil beam with optical vortex or Laguerre-Gauss mode (doughnut mode).

The light-source may furthermore exhibit a focusing lens system which has been arranged between the optical control element and the specimen holder. The focusing lens system may comprise a focusing lens or a focusing-lens system for forming the pencil beam (with the defined beam within the specimen holder). Preferentially, the focusing lens system exhibits a telescopic lens system and a focusing lens. To the advantage of a higher resolution, the focusing lens system can widen the beam (downstream of the rasterisation mirrors). In this way, a width of the rasterisation mirrors may be smaller than the beam width. The focusing lens system can radiate the pencil beam into the specimen holder with a larger numerical aperture. In this way, an incident numerical aperture of $NA_E=0.2$ is attainable. (The incident numerical aperture, $NA_E$, is not to be confused with the acquired numerical aperture, NA.) A first focal plane of the focusing lens system may include (substantially) a position of the rasterisation mirror. A second focal plane of the focusing lens system may include (substantially) a position within the specimen holder, preferentially a position of the beam waist or of the axis of rotation within the specimen holder.

The apparatus may furthermore include a computing unit which has been connected to or is capable of being connected to the signal generator of the detector unit for the purpose of transmitting a data record comprising intensity data from the signal generator to the processing unit. The intensity data may represent intensities of the acquired scattered radiation. The optical control element may have been designed to offset (controlled by the computing unit) the pencil beam (stepwise or continuously) into a plurality of different measuring positions. The data record may be a raster data record which comprises intensity data relating to each of the plurality of measuring positions.

The apparatus may furthermore include a motor (controlled by the computing unit) for (stepwise or continuous) rotation of the specimen holder and of the light-source relative to one another into a plurality of different rotary positions. The data record may be a tomographic data record which comprises a raster data record relating to each of the plurality of rotary positions.

The computing unit may furthermore have been designed to reconstruct, on the basis of the tomographic data record, a sectional image or a spatial image. The reconstructed image may represent a scattering coefficient (of a specimen in the specimen holder) and/or (in supplement) an extinction coefficient (of the specimen in the specimen holder). The reconstruction may comprise an inverse Radon transformation. Alternatively or additionally, the reconstruction may comprise an iterative reconstruction. The computing unit may furthermore have been designed to correct an extinction of the pencil beam in accordance with the (integral) Lambert-Beer law, or to take it into consideration in the reconstruction.

The object is furthermore achieved by a process for tomographic image acquisition having the process steps of Claim 19.

BRIEF DESCRIPTION OF THE DRAWINGS

Further advantages and features of the invention will become apparent from the exemplary embodiments described below with reference to schematic drawings. Shown are.

DETAILED DESCRIPTION

Reference symbols, relating to various exemplary embodiments, having the same two final numerals relate to similar components (interchangeable among the exemplary embodiments).

Figure 1:
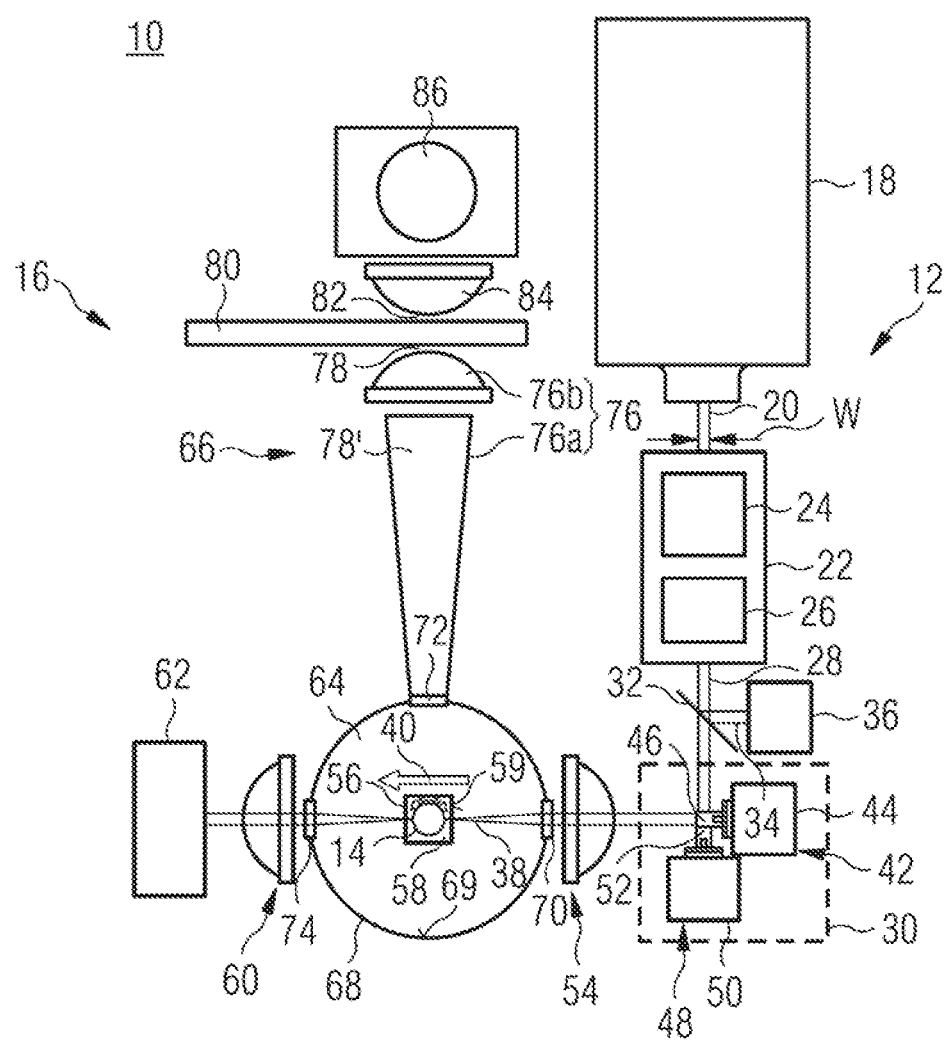
FIG. 1 a top view of a first exemplary embodiment of the apparatus for tomographic image acquisition with an integrator, FIGS. 2a and 2b a top view and a side view, respectively, of a second exemplary embodiment of the apparatus for tomographic image acquisition with a reflecting specimen vessel, FIG. 3 a top view of a third exemplary embodiment of the apparatus for tomographic image acquisition with a reflector, FIG. 4 a top view of a fourth exemplary embodiment of the apparatus for tomographic image acquisition with several scattered-radiation collectors, FIG. 5 a top view of a fifth exemplary embodiment of the apparatus for tomographic image acquisition with a collimator recess, and FIG. 6 a flow chart of a process for tomographic image acquisition.

FIG. 1 shows an apparatus denoted generally by 10 for tomographic image acquisition. The apparatus 10 includes a light-source 12, a specimen holder 14 and a detector unit 16.

The light-source 12 includes a radiation-source 18 which emits an at least substantially spatially coherent raw beam 20. In the exemplary embodiment that is shown, the radiation-source 18 is a laser. If a beam width w of the raw beam 20 made available by the radiation-source 18 is too small, a beam-shaping lens system 22 includes a telescopic lens system 24 which widens the raw beam 20.

Irrespective of the radiation-source 18 employed, the beam-shaping lens system 22 includes a variety of diaphragms and phase masks 26 which change the raw beam 20 into a shaped beam 28. The beam-shaping lens system 22 enables imaging properties of the apparatus 10 to be varied. In this way, a resolution attained with the apparatus 10 can be increased or can be adapted in stepless manner, in particular taking into consideration a specimen-dependent maximal beam intensity. Above and beyond this, the diaphragms or phase masks 26 project the shaped beam 28 into an optical control element 30 of the light-source 12, arranged downstream in the beam path.

Optionally, a beam-splitter 32 may have been incorporated between the beam-shaping lens system 22 and the optical control element 30, which branches off a partial beam 34 from the shaped beam 28 into a reference detector 36. In the exemplary embodiment that is shown, a photodiode is employed as reference detector 36. The reference detector 36 monitors, on the one hand, the stability of the laser of the radiation-source 18. On the other hand, the reference detector 36 (as signal generator of a control circuit which is not shown) serves for selective intensity modulation of the radiation-source 18. In connection with the intensity modulation, in principle an increased intensity for illuminating the specimen is assumed. A detector-side dynamic range (of each of the detectors described below, in particular of the detector unit 16) has been exhausted if the radiation-source 18 evokes a detector-side overload or signal saturation. The intensity of the radiation-source 18 is selectively reduced so far for individual partial acquisitions (ideally, for each of the measured positions, described below, of the optical control element 30) until no detector-side overload is present. By virtue of the intensity modulation, a generation-side dynamic range (determined by the radiation-source 18 and the reference detector 36) is multiplied by the detector-side dynamic range to yield a (extended and lower-noise) dynamic range of the acquisition.

The optical control element 30 enables the course of a pencil beam 38 through the specimen holder 14 to be offset substantially parallel to the beam direction 40. A (transverse) measuring position of the optical control element 30 will be described in a rectangular coordinate system at right angles (or perpendicular) to the beam direction 40 by an x-offset and a y-offset. In a simplified embodiment, the optical control element 30 includes only an x-control element 42 with an x-actuator 44 which tilts an x-rasterisation mirror 46. An x-swivel axis of the x-tilting corresponds to the y-axis of the transverse coordinate system (and is consequently perpendicular to the beam direction 40). In the exemplary embodiment that is shown, the optical control element 30 furthermore includes a y-control element 48 with a y-actuator 50 which tilts a y-rasterisation mirror 52 about a y-swivel axis (corresponding to the x-axis of the transverse coordinate system). In an alternative embodiment (not shown) of the optical control element 30, a single rasterisation mirror is tilted by the x-actuator 44 and the y-actuator 50 about the x-swivel axis and the y-swivel axis, respectively. By way of actuators 44, 50, use is made of galvanometric drives (also designated as "galvos" or "galvo scanners"). The actuators 44 and 50 each include an automatic control system which acquires a rotary mirror position of the rasterisation mirrors 46 and 52, respectively, and regulates a current for attaining the desired offset.

The optical control element 30, more precisely the last of the two rasterisation mirrors 46, 52 in the beam path, is located in a rear first focal plane of a focusing lens system 54 of the light-source 12. The optical control element 30 deflects (by reflection) the beam path around an optical axis of the focusing lens system 54. The focusing lens system 54 has been designed to project the pencil beam 38 into the specimen holder 14 with a beam waist in the centre of a section of the pencil beam 38 within the specimen holder (corresponding to a second focal plane of the focusing lens system 54). By deflection (by means of the last rasterisation mirror 52 in the beam path) in the first focal plane of the focusing lens system 54, a telecentric projection of the pencil beam 38 (into the specimen holder 14) is obtained. This permits a parallel offset also for large deflection angles (corresponding to a doubled tilt angle of the rasterisation mirror 46, 52). Deviations from a parallel (to the beam direction 40) beam offset could make a later image reconstruction more difficult. The parallel offset of the pencil beam enables a quick (tomographic) image reconstruction by inversion of a Radon transformation. As an alternative to the tilting of the at least one rasterisation mirror 46, 52, the light-source can be displaced (with respect to the specimen holder 14).

In an embodiment, not shown, of the light-source 12 without telecentric arrangement (of the optical control element 30 and of the focusing lens system 54), a tomographic image acquisition is likewise attainable. In this connection, the offset of the pencil beam 38 brought about by the optical control element 30 is given the beam direction 40, at least insofar as the (transverse) offset (in the specimen holder 14) is small in comparison to the (optical) path length between the optical control element 30 and the specimen holder 14. In other words, parallelism of the pencil-beam offset in the specimen holder is obtained (by approximation) for small tilt angles of the optical control element 30. Furthermore, a (tomographic) image can also be reconstructed in the case of greater fanning of the pencil beam 38 (at the location of the specimen holder around the ideal beam direction 40 in the case of various measuring positions) by adapted direct or iterative processes.

A first embodiment (not shown) of the specimen holder 14 has been designed to position a specimen directly. To this end, the specimen holder 14 may exhibit a clip for the specimen, a tightening screw for clamping the specimen, or an adhesive surface for attaching the specimen. In this way, large specimens can be (slowly) rotated. A second embodiment (not shown) of the specimen holder 14 has been designed for positioning a gel volume (preferentially an agarose gel). The specimen can be enclosed in the gel volume (by casting and gelation). The third embodiment of the specimen holder 14, which is shown, includes a glass tube filled with a refractive-index-adapted liquid, into which the specimen can be drawn. In principle, a refractive index of the specimen can be adapted as an alternative or in supplement to an adaptation (each adaptation described herein) of the refractive index of the specimen environment. For techniques for adjusting the refractive index of the specimen, reference is made to EP 1 520 173 B1 (and, in particular, paragraphs [0013] ff therein).

The specimen holder 14 has been rotatably arranged in a specimen vessel 56, preferentially a cell. A liquid (which in the case of the third embodiment of the specimen vessel 14 coincides, at least with regard to its refractive index, with the aforementioned liquid) adapted to the specimen as regards its refractive index is located between the specimen holder 14 and the specimen vessel 56. The rotation relates to a relative rotation between, on the one hand, the specimen holder 14 and, on the other hand, at least the light-source 12 and the specimen vessel 56. In principle, a "boundary" or "interface" of the rotation extends between the specimen holder 14 and the specimen vessel 56 (particularly since the specimen vessel 56 may exhibit entrance windows and exit windows, described below, for the pencil beam 38, the location of which, with a view to simplified reconstruction, should not be rotated in relation to the pencil beam 38). An axis of rotation of the rotation is vertical (perpendicular to the plane of the drawing of FIG. 1, corresponding to the y-direction). The (imaginary) axis of rotation of the rotation extends through the specimen holder 14. In the exemplary embodiment shown in FIG. 1, the specimen holder 14 is cylindrical and the axis of rotation coincides with the cylinder axis. In a first variant, an electric drive, preferentially a stepper motor (corresponding to the stepper motor denoted by 88 in the exemplary embodiment shown in FIG. 2), has been provided for rotating the specimen holder 14. The light-source 12 and the detector unit 16 are stationary. In a second variant, the electric drive has been designed to rotate all the other components of the apparatus 10 in relation to the unmoved specimen holder 14.

Particularly for a mobile apparatus 10, all the components except the rasterisation mirrors 46, 52 and the specimen holder 14 have been rigidly connected to one another. Furthermore, in the second variant a stationary or immovable specimen can be examined, for instance a rooted plant, whereby the specimen vessel 56 and the entire light-source 12 rotate about the specimen. In this connection, with a view to the examination of larger specimens the specimen vessel 56 (and in the case of stationary specimens, even the specimen holder 14) can be dispensed with.

With the apparatus 10 a non-transparent specimen can also be acquired tomographically. The scattered light acquired in positionally unresolved manner can in this case be reflected substantially at the surface of the non-transparent specimen or scattered by any other effect. The non-transparent specimen may have a tomographically acquirable surface structure. For example, the surface of the specimen may exhibit an at least partially transparent coating. The scattered light may comprise scattered components and reflected components. The scattered portion may have been brought about by scattering of the pencil beam in the coating. The reflected portion may have been brought about by reflection of the pencil beam or of the forward-scattered pencil beam at the surface of the non-transparent specimen. A screw is an example of the non-transparent specimen.

With a view to spatial positioning of the specimen, in a further first variant or in the aforementioned first variant the specimen holder 14 (and, synchronously therewith, the specimen vessel 56) is capable of being transported by means of a stage micrometer in all three directions (i.e., in the x-direction, the y-direction and the beam direction 40). In a further second variant or in the aforementioned second variant, the specimen holder 14 (and the specimen vessel 56) is stationary, and the light-source 12 and the detector unit 16 (or all the other components except the specimen holder 14 and the specimen vessel 56) can be moved in all three directions. In a simplified exemplary embodiment (of the first variant or of the second variant), the transportability has been restricted to the vertical direction (i.e. the y-direction).

A tilting of the axis of rotation is present if
(A) the axis of rotation is not perpendicular to the beam direction 40, or
(B) the axis of rotation is not perpendicular to the x-direction of the optical control element 30.

In general, the tilting of cases (A) and (B) is present in combined manner. In other words, a tilting is present if the axis of rotation is not spatially parallel to the y-axis.

The tilting may make the later image reconstruction more difficult or cause tilting artefacts in the reconstructed image. With a view to adjustment of the apparatus 10, in particular with a view to compensating for the tilting, adjusting mechanisms have been provided which enable a swivelling of the axis of rotation (and hence also of the specimen holder 14) relative to the beam direction 40. The aim of the adjusting mechanisms is to align the axis of rotation parallel to the y-axis as direction in space.

With regard to the tilting of case (A), the optical control element 30 and the focusing lens system 54 are displaceable relative to one another by means of a first adjusting mechanism. In this way, the focusing lens system 54 can be displaced perpendicular to the optical axis of the focusing lens system 54. Alternatively, the optical control element 30 can be displaced perpendicular to the optical axis of the focusing lens system 54. (In principle, it is also possible to displace the entire light-source, with the exception of the focusing lens system 54.) By virtue of the displacement in the y-direction, a rising or falling course of the pencil beam with respect to the y-direction can be set. In this way, a right angle between the axis of rotation and the beam direction 40 can be set (in the plane spanned by the beam direction 40 and the y-direction). Alternatively or in supplement to the displacement, the first adjusting mechanism enables the axis of rotation to be swivelled about the x-axis. Also, a perpendicular course of the pencil beam relative to the axis of rotation can be set thereby (in the plane spanned by the beam direction 40 and the y-direction).

With regard to the tilting of case (B), a second adjusting mechanism enables the axis of rotation (and hence also the specimen holder 14) to be swivelled about the optical axis of the focusing lens system 54. Alternatively, the optical control element 30 can also be swivelled about the optical axis of the focusing lens system 54. As a result, the axis of rotation can be caused to coincide with the y-direction. Furthermore, the tilting of case (B) (unlike the tilting of case (A)) is also capable of being compensated by a numeric rotation of the raw data acquired (at a rotary position) in the xy-plane.

Inasmuch as tilting is avoided in the optical set-up, a subsequent reconstruction by layers can be decoupled. A "layer" encompasses all acquisitions at measuring positions with the same position in the y-direction (i.e. at the same "height"). The reconstruction of the tomographic image acquisition can be parallelised for various layers. To the extent that tilting is present, dependencies (between acquisitions at various positions in the y-direction) arise which do not fundamentally preclude a tomographic image reconstruction. However, consideration of the dependencies can increase the complexity of a reconstruction algorithm.

To the extent that two rasterisation mirrors 46, 52 are employed in the optical control element 30, in a simple embodiment (of the optical control element) the optical control element 30 may have been arranged in such a way with respect to the focusing lens system 54 that the first focal plane of the focusing lens system 54 is situated between the rasterisation mirrors 46 and 52. In this way, a fanning of the pencil beam 38 (i.e. a deviation from an ideally uniform beam direction 40) can be minimised. Alternatively, either the x-rasterisation mirror 46 or the y-rasterisation mirror 52 may have been arranged in the first focal plane of the focusing lens system 54. In this way, the fanning can be restricted to the rasterisation in the y-direction or in the x-direction (and taken into consideration by the reconstruction algorithm). A further adjusting mechanism is provided, which is able to move the two rasterisation mirrors 46 and 52 (in the x-direction and in the beam direction 40). An extended embodiment of the optical control element 30 includes the aforementioned relay lens system. By means of the relay lens system, both the x-rasterisation mirror 46 and the y-rasterisation mirror 52 can be arranged in a respective focal plane (of the relay lens system). The last rasterisation mirror 52 in the beam path is situated, in addition, in the first focal plane of the focusing lens system 54. In this way, a fanning in the x-direction and in the y-direction can be minimised. For simplified embodiments, individual adjusting mechanisms or all adjusting mechanisms are dispensed with.

The volume between the specimen holder 14 and the specimen vessel 56 has been filled up with a liquid 58 (at the height of the pencil beam 38) approximated to the refractive index of the specimen holder 14 (and of the specimen therein to be examined). The liquid 58 serves as immersion liquid. Inasmuch as the liquid 58 wets the specimen holder 14, the (generally curved) surface of the specimen holder 14 as optical interface (as regards undesirable refraction or scattering) is almost eliminated. The beam which generally is weakly focused by the focusing lens system 54 is projected by a smooth glass surface 59 of the specimen vessel 56 into the specimen vessel 56. "Smooth" means that the glass surface 59 is flat (i.e. not curved). In addition, "smooth" may encompass a slight (as far as possible) surface roughness.

Radiation transmitted by the specimen is projected by a second focusing lens system 60 onto a transmission photodetector 62. A first focal plane of the second focusing lens system 60 coincides with the second focal plane of the first focusing lens system 54. A rear second focal plane of the second focusing lens system 60 coincides with a position of the transmission photodetector 62. In this case, an exact positioning of the focal planes of the second focusing lens system 60 is not required. The demands made of the imaging properties of the second focusing lens system 60 are less than those of the first focusing lens system 54.

To the advantage of a larger dynamic range covered by the transmission photodetector 62, and with a view to improving the dynamic range of the acquisition (without losses of speed in the course of image acquisition), the transmission photodetector 62 has a non-linear response, preferentially a logarithmic response. The "speed" of the image acquisition relates, in particular, to the exposure-time for each measuring position. Moreover, intensities that have been made logarithmic are more advantageous (since they are immediately convertible) output data for computer-aided reconstruction.

In conjunction with the transmission detector unit 60, 62, furthermore dark-field microscopy, polarisation microscopy, interference contrast microscopy (which is also designated as differential interference contrast microscopy or DIC microscopy) or phase contrast microscopy can be realised.

In a simplified exemplary embodiment, the second focusing lens system 60 and the transmission photodetector 62 are dispensed with. In an additional exemplary embodiment, furthermore a diaphragm has been provided between the second focusing lens system 60 and the transmission photodetector 62 for the purpose of limiting the forward scattering. Inasmuch as (instead of the transmission photodetector 62) the diaphragm has been arranged in the (rear) second focal plane of the second focusing lens system 60, the forward scattering emanating from the entire section of the pencil beam in the specimen holder 14 can be acquired separately. In the case of non-resonant fluorescence, transmission and forward scattering can furthermore be separated by a dichroic filter.

Scattered radiation 64 emanates from the specimen by reason of the incident pencil beam 38. Often, the scattered radiation 64 emitted from the specimen is distributed almost isotropically (i.e. in all directions substantially uniformly). In the case of fluorescent radiation by way of scattered radiation 64, the radiation-source 18 has been designed to generate a pencil beam 38 which excites one or more selected transitions of a fluorophore (functionally or structurally marking the specimen) in the specimen. The intensity of the re-emitted scattered radiation 64 is acquired in the form of an acquired scattering-intensity distribution, $I(x,y,\pi)$, at various measuring positions in the x- and y-directions as well as various rotary positions. Generally, the acquired scattering-intensity distribution contains information (accessible through the tomographic reconstruction) about the fluorophore concentration, $\rho(x,y,z)$, in the specimen (in the case of fluorescent radiation) or the scattering coefficient, $\sigma(x,y,z)$, of the specimen (in the case of a different scattering mechanism). For a given rotary position n, the (integral) scattering-intensity distribution $I(x,y,\pi)$ is an item of 2-dimensional information which results from the 3-dimensional scattering intensity $\sigma(x,y,z)$ (substantially by projection in the beam direction 40 or summation along the pencil beam 38).

The scattered radiation 64 is acquired integrally by means of the detector unit 16. The integral acquisition of the scattered radiation 64 includes the positionally unresolved and directionally unresolved acquisition of the scattered radiation 64 brought about by the pencil beam 38.

The detector unit 16 includes a scattered-radiation collector 66 for integral acquisition of the scattered radiation 64 within a solid angle that is as large as possible about the specimen holder 14. A numerical aperture NA/n (normalised to the refractive index) corresponds to the acquired solid angle. With a view to integral acquisition of the scattered radiation 64, the specimen holder 14 (and the specimen vessel 56) have been arranged in the centre of an integrator 68 of the scattered-radiation collector 66. The integrator 68 includes a capsule which is highly reflecting and strongly light-scattering in the interior. An inner surface 69 of the integrator 68 has been coated with barium sulfate (or with another scattering medium). In a simpler embodiment of the integrator 68, the inner surface 69 exhibits a rough base, onto which a metal layer (preferentially consisting of silver) has been vapour-deposited. The exemplary embodiment shown in FIG. 1 employs by way of integrator 68 an Ulbricht sphere. By virtue of the (multiple) scattered reflection, the scattered radiation (emanating from the specimen) is homogeneously distributed in the interior of the integrator 68. The homogeneity has in consequence (given almost lossless scattered reflection) several technical aspects. On the one hand, an exact positioning of the specimen holder 14 (and of the specimen vessel 56) in the centre of the integrator 68 is not necessary in the course of design and manufacture of the apparatus 10. In this way, hollow bodies differing from a spherical shape are suitable by way of integrator 68. In a compact embodiment, the integrator 68 is realised by the appropriately coated specimen vessel 56. On the other hand, the intensity of the scattered radiation at all apertures 70, 72, 74 of the integrator 68 is substantially of the same magnitude.

The proportion of the scattered radiation 64 that emerges at the measuring aperture 72 is connected with the entire scattered radiation 64 in accordance with an aperture ratio of the measuring aperture 72 to an entire aperture area (comprising the apertures 70, 72 and 74) of the integrator 68. In this way, with a view to integral acquisition of the scattered radiation 64, the entire scattered radiation 64 can be determined by acquiring the scattered radiation emerging at the measuring aperture 72.

For a high signal-to-noise ratio, the measuring aperture 72 of the integrator 68 has been chosen to be as large as possible, and all the other apertures 70, 74 in the integrator 68 have been chosen to be as small as possible. In order to improve the aperture ratio, in an optimised variant of the exemplary embodiment merely an x-control element 42 has been provided (as described above), and the illumination aperture 70 is a slit that is as narrow as possible in the y-direction (and extending in the x-direction). Similarly, the transmission aperture 74 is a slit (as narrow as possible in the y-direction) in the x-direction. A slit height $\Delta y$ amounts to 100% to 500%, preferentially about 200%, of a beam width of the pencil beam 38 at the slit. In an exemplary embodiment, the illumination aperture 70 and the transmission aperture 74 are respectively a slit with a height of $\Delta y=0.5$ mm and a width of $\Delta x=12$ mm, and the measuring aperture 72 is square with edges having a length of 10 mm. Consequently, for the exemplary embodiment an ideal efficiency corresponding to the aperture ratio amounts to 100/112=89.3%.

In order also to acquire measuring positions with varying y-offset in the case of the aperture ratio improved through a slit shape, a y-actuator (as an alternative to the y-control element 48 with the y-rasterisation mirror 52) is employed which moves the specimen holder 14 (advantageously synchronously with the specimen vessel 56) in the y-direction corresponding to the desired y-offset (up or down). In an alternative variant of the exemplary embodiment, the specimen holder 14 (and the specimen vessel 56) is stationary in the y-direction, with the light-source 12 and the detector unit 16 (or all the other components except the specimen holder 14 and the specimen vessel 56) being transportable up and down in the y-direction.

For technical reasons, an integrator 68 that is as small as possible is to be preferred to a larger integrator 68, the advantages of which may include smaller scattering-reflection losses on the smaller inner surface 69 and narrower slits at the illumination aperture 70 and at the transmission aperture 74.

The measuring aperture 72 should be equal in size to or larger than the specimen, the specimen holder 14, or the specimen vessel 56. (A possible specimen size may amount to about 2 mm. In the case of specimens of greater dimension, the measuring aperture 72 may also be smaller than the specimen size.) More precisely, an edge length of the square measuring aperture 72 should be greater than a length of the specimen holder 14 in the beam direction 40. Since the homogenised scattered radiation 64 in the integrator 68 also falls onto the specimen holder 14, in this way a portion of multiply-scattered radiation at the measuring aperture 72 (and a corresponding undesirable background signal) can be suppressed. In the case of non-resonant fluorescent radiation, the wavelength shift in addition suppresses the situation where fluorescent radiation excites further fluorescence.

In a further development of the exemplary embodiment, a slit width of the illumination aperture 70 and of the transmission aperture 74 is variable. Furthermore, optical internals in the integrator 68 or lens systems in the apertures 70, 72, 74 have been designed to reduce losses further at the apertures 70, 72, 74.

The scattered-radiation collector 66 furthermore includes a first collimator 76 which is able to reduce the divergence of the scattered radiation emerging from the measuring aperture 72. The first collimator 76 includes either a tapered light guide (tapered light pipe) 76a, a strongly refracting lens 76b, in particular a condenser lens; a concave mirror (not shown) with a central aperture; or a combination comprising two or more of these elements. By way of light guide, a reflectively coated (silvered) optical hollow-core conductor or a dielectric optical waveguide (utilising the total reflection) is capable of being employed. The first collimator 76 shown in the exemplary embodiment represented in FIG. 1 includes the optical hollow-core conductor 76a and the lens 76b. The divergence of the partly collimated scattered radiation 78' at the output of the optical hollow-core conductor 76a is further reduced by the lens 76b to yield the collimated scattered radiation 78.

In an alternative (not shown), the measuring aperture 72 and the light guide 76a have been replaced by a glass-fibre bundle. The glass-fibre bundle comprises a plurality of glass fibres which extend in stellate manner (i.e. radially) from a sphere (to this extent, replacing the integrator 68). The ends of the glass fibres receiving the scattered radiation 64 from the specimen holder 14 are uniformly distributed over the inner surface 69 of the sphere. The glass fibres have been designed to bring the scattered radiation to a focus in a plane 64. Also in this alternative, in this way partly collimated scattered radiation 78' is obtained which is projected by one of the aforementioned elements of the collimator 76 to yield the collimated scattered radiation 78.

The collimated scattered radiation 78 exhibits a reduced divergence with a residual divergence. A sufficiently low residual divergence enables a dichroic filter to be applied to the collimated radiation 78. Most filters are capable of being applied downstream of a first collimator 76 which attains a residual divergence of less than ±30°. When use is made of coloured-glass filters, the scattered radiation 64 is not subject to any appreciable divergence restriction. In this way, in simplified exemplary embodiments with coloured-glass filters a simple first collimator 76 (with only one of the elements) or no first collimator 76 has been provided.

The collimated scattered radiation 78 optionally passes through one filter of several filters which have been combined in a filter-option unit 80, taking the form of a filter disc or filter drawer, of the detector unit 16. In the case of fluorescent radiation, spectral regions of high transparency of the filters are each tuned to a fluorescence transition of one or various fluorophores. A resulting filtered scattered radiation 82 exhibits the intensity to be measured.

In additional exemplary embodiments, dichroic mirrors (not shown) are employed for the purpose of splitting various colour components into various beam paths. The dichroic mirrors are arranged in supplement to, or instead of, the filter-option unit 80. This enables a simultaneous acquisition of the various colour components contained in the scattered radiation 64.

The detector unit 16 furthermore includes a second collimator 84 and a signal generator 86 (arranged in a rear focal plane of the second collimator 84) for photodetection. In the exemplary embodiment shown in FIG. 1, the second collimator lens 84 is a converging lens, preferentially a condenser lens. With a view to optimising a quantum yield, the second collimator 84 focuses the filtered scattered radiation 82 onto the signal generator 86, without exceeding the numerical aperture thereof. In the exemplary embodiment shown in FIG. 1, the signal generator 86 is a photomultiplier tube. For a beam intensity acting on the specimen that is as low as possible, the photomultiplier tube exhibits a high responsivity (and quantum yield).

Furthermore, the signal generator 86 is displaceable (at right angles to the direction of the filtered scattered radiation 82), in order to illuminate optimally an optically sensitive surface (detecting surface) of the signal generator 86. In this way, the detector unit 16 can guide the scattered radiation 64 of the measuring aperture 72 efficiently onto the detector surface.

The following processes are capable of being implemented with the apparatus 10 which has been described: FLIM (fluorescence-lifetime imaging microscopy), whereby the fluorescence lifetime and the light propagation time in the integrator 68 have been matched to one another with a view to avoiding restrictions by virtue of diffuse scattering in the integrator 68; MPM (multi-photon microscopy); FRET (fluorescence resonance energy transfer); FRAP (fluorescence recovery after photobleaching); STED (stimulated emission depletion), whereby after the pencil beam 38 by way of exciting beam a "tube beam" by way of exclusion beam with substantially cylindrically symmetrical intensity distribution is radiated in; FLIP (fluorescence loss in photobleaching); so-called super-resolution microscopy; scattered-light microscopy; possibly the following may also be capable of being implemented: STORM (stochastic optical reconstruction microscopy) and FCS (fluorescence correlation spectroscopy).

Figure 2A:
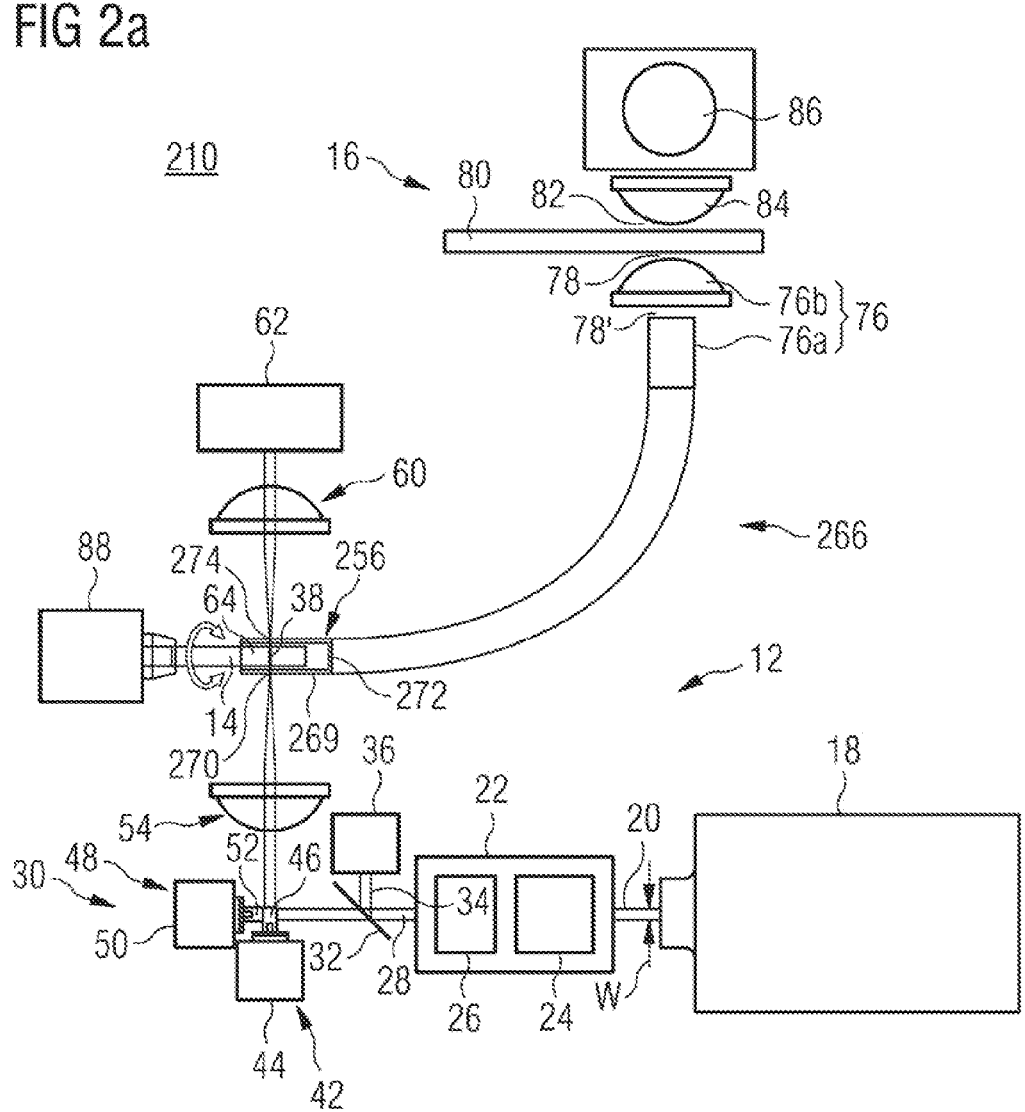

FIG. 2 shows a second exemplary embodiment of an apparatus 210 for tomographic image acquisition. For components of the second exemplary embodiment having the same reference symbols as in the first exemplary embodiment, what was described above applies correspondingly, particularly as regards their properties, constitution, function and their interaction.

The second exemplary embodiment differs from the first exemplary embodiment in that no separate integrator 68 has been provided for integrating and homogenising the acquired scattered radiation 64. In other words, with a view to integral acquisition of the scattered radiation 64 a scattered-radiation collector 266 does not include an integrator 68. The beam-transparent specimen vessel 256 exhibits a reflecting surface 269 on all the side surfaces (i.e. on all the surfaces except a transparent bottom surface 272). The reflecting surface 269 undertakes the function and action of the (diffusely reflecting) inner surface 69. In this way, the specimen vessel 256 can also undertake the function and action of the integrator 68.

A simple first embodiment of the specimen vessel 256 is an uncoated glass cell. Scattered radiation 64, which has a tendency to be radiated to the bottom surface 272 of the uncoated cell, is conducted by total reflection at the cell/air boundary layer to the bottom surface 272. In this way, a proportion of about 12.5% of the scattered radiation 64 is capable of being acquired. The proportion results by virtue of the angle of total reflection at the wall of the specimen vessel 256 (i.e. at the interface from cell to air). In a second embodiment of the specimen vessel 256, a base body made of glass (on the outside or on the inside) exhibits a layer of barium sulfate or a metal layer by way of reflecting surface 269, as described above in connection with the inner surface 69. In a third embodiment of the specimen vessel 256, the side surfaces of a metallic base body act as reflecting surface 269. In a fourth embodiment of the specimen vessel 256, the latter tallies with the specimen vessel 56 and has furthermore been set in accurately fitting manner into a mirror box (not shown) having reflecting surfaces 269.

With a view to radiating the pencil beam 38, and optionally for transmission detection, the specimen vessel 256 exhibits an illumination aperture 270 and a transmission aperture 274, respectively. The illumination aperture 270 and, where appropriate, the transmission aperture 274 correspond (functionally) to aperture 70 and to aperture 74, respectively. As described above in connection with apertures 70, 72, 74, with a view to minimising radiation losses apertures 270 and 274 take the form of narrow slits in the x-direction, and the optical control element 30 rasterises the pencil beam 38 only in the x-direction. For measuring positions with y-offset, the specimen holder 14 can be moved relative to all other components in the y-direction, whereby the specimen holder 14 or the other components are stationary, as has been described above for the first exemplary embodiment. The reflecting surface 269 exhibits opposing beam-transparent slits by way of apertures 270 and 274. In the case of the base body made of glass, apertures 270, 274 are uncoated. In the case of the metallic base body, apertures 270, 274 include plane-parallel windows. In the case of fluorescent radiation by way of scattered radiation, with a view to further reduction of radiation losses the windows exhibit a dichroic layer transmitting the exciting radiation (of the pencil beam 38) and reflecting the fluorescent radiation, or consist of a plane-parallel birefringent crystal (with such optical properties). In the fourth embodiment with the mirror box, apertures 270, 274 are through-holes of the mirror box.

The bottom surface 272 is transparent to the scattered radiation 64. In the case of the base body made of glass, the bottom surface 272 is uncoated. In the case of the metallic base body, the bottom surface 272 includes a plane-parallel window. In the fourth embodiment with the mirror box, the mirror box is open on the bottom surface 272.

The fifth embodiment of the specimen vessel 256 shown in FIG. 2 for fluorescent radiation by way of scattered radiation includes a transparent base body which exhibits a dichroic layer on the side surfaces. Alternatively or in supplement, the side surfaces of the specimen vessel consist of a dichroic filter or an interference filter. In this way, the side surfaces of the specimen vessel 256 have been designed to transmit the exciting radiation (of the pencil beam 38) and to reflect the fluorescent radiation. In this way, a proportion of the scattered radiation 64 of about 50% or more can be acquired. With regard to the fluorescent radiation (i.e. the scattered radiation 64), the side faces act as reflecting surface 269. Since the side faces are transparent with regard to the exciting radiation (of the pencil beam 38), the side surfaces in addition enable the entrance and exit of the pencil beam 38. That is to say, the entire side surfaces are available by way of illumination aperture 270 or transmission aperture 274. The control element 30 has been designed for rasterisation (i.e. offset) of the pencil beam in the x-direction and in the y-direction. Without radiation losses, windows (in particular, slits) can be dispensed with. A transportability of the specimen holder 14 in the y-direction is not required.

In all the embodiments of the specimen vessel 256, by reflection (or total reflection) of the scattered radiation 64 on the reflecting surface 269 the scattered radiation 64 is guided to the bottom surface 272. With a view to integral acquisition of the scattered radiation 64, a portion of the scattered radiation 272$b$ emerging through the bottom surface 272 is acquired. The bottom surface 272 corresponds (functionally) to the measuring aperture 72. The proportion of the scattered radiation emerging through the bottom surface 272 with respect to the total scattered radiation can be determined as described above in connection with the measuring aperture 72. Furthermore, the proportion of the scattered radiation emerging through the bottom surface 272 can be determined by a reflection angle at which the scattered radiation is reflected from the reflecting surface 269. To the extent that the reflection at the reflecting surfaces 269 includes total reflection (as in the first and fifth embodiments of the specimen vessel 256), the angle of reflection for determining the proportion is a total reflection angle at the reflecting surface 269.

FIG. 2$b$ shows, furthermore, an optional second detector unit 16' which has been described in more detail below in connection with a fourth exemplary embodiment of an apparatus 410. With a view to enlarging the acquired solid angle, the detector units 16, 16' of the various exemplary embodiments can be combined.

In order (with any of the embodiments of the specimen vessel 256) to couple more than 12.5% of the scattered radiation out from the specimen vessel 256, the first collimator 76 of the scattered-radiation collector 266 is in direct (refractive-index-adapted) optical contact with the bottom surface 272. As described above, the first collimator 76 includes a tapered light guide 76$a$ on the specimen side.

All the further features of the second exemplary embodiment correspond to those of the first exemplary embodiment. In particular, mutually corresponding assemblies 12, 14, 16 and the components thereof have the same degrees of freedom.

The following processes are capable of being implemented with the apparatus 210 which has been described: FLIM (fluorescence-lifetime imaging microscopy); MPM (multi-photon microscopy); FRET (fluorescence resonance energy transfer); FRAP (fluorescence recovery after photobleaching); STED (stimulated emission depletion), whereby after the pencil beam 38 by way of exciting beam a "tube beam" by way of exclusion beam with substantially cylindrically symmetrical intensity distribution is radiated in; FLIP (fluorescence loss in photobleaching); so-called superresolution microscopy; scattered-light microscopy; possibly the following may also be capable of being implemented: STORM (stochastic optical reconstruction microscopy) and FCS (fluorescence correlation spectroscopy).

Figure 3:
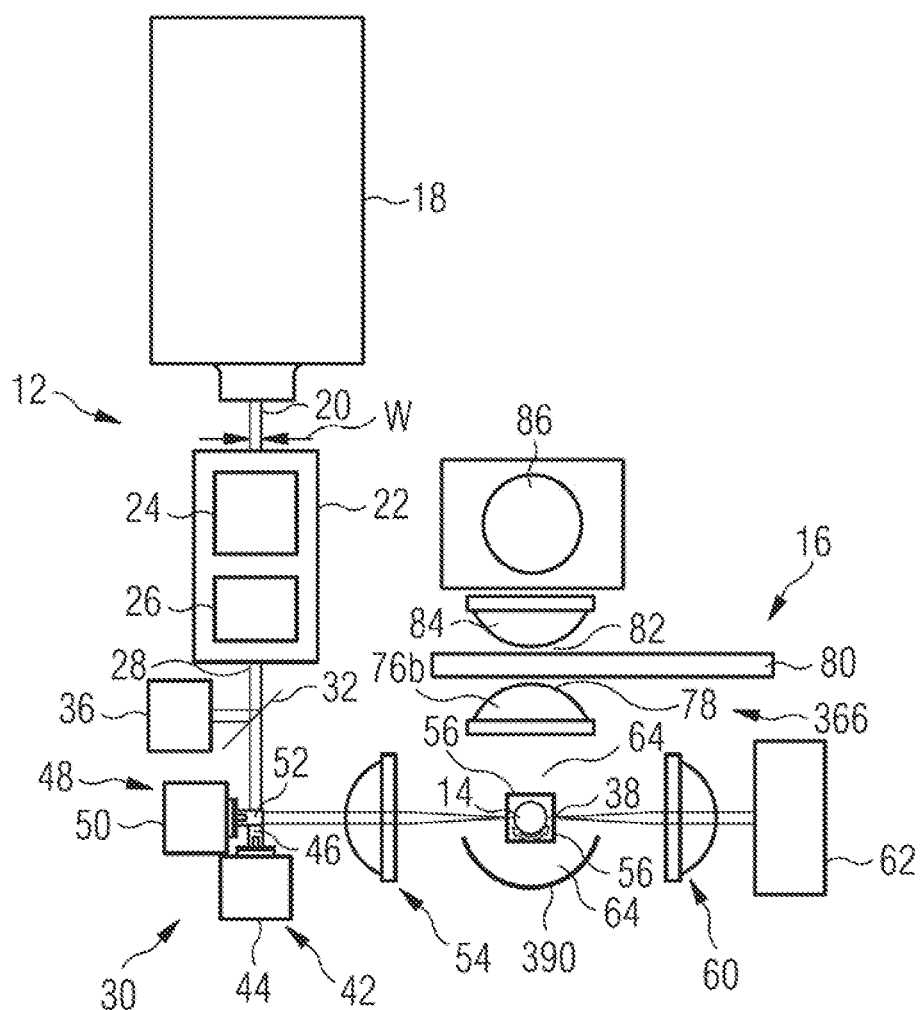

FIG. 3 shows a third exemplary embodiment of an apparatus 310 for tomographic image acquisition. For components of the third exemplary embodiment having the same reference symbols as in the first or second exemplary embodiment, what was described above applies correspondingly, particularly with regard to their properties, constitution, function and their interaction.

The third exemplary embodiment differs from one of the preceding exemplary embodiments in that the scattered radiation 64 is collected (i.e. integrated) directly with a first collimator. In other words, with a view to integral acquisition of the scattered radiation 64, a scattered-radiation collector 366 does not include a light guide 76a. The scattered-radiation collector 366 includes by way of first collimator a lens 76b, as described above. In addition, the scattered-radiation collector 366 includes a reflector 390. The specimen holder 14 and the specimen vessel 56 have been arranged between the reflector 390 and the lens 76b. The specimen holder 14, more precisely, the axis of rotation, is situated in a focal plane of the lens 76b. By way of reflector 390, a spherical concave mirror or a plurality of retroreflectors (also designated as "cat's-eye") has/have been employed. In the latter case, the apparatus 310 is particularly easy to adjust. In the case of the spherical concave mirror, a sphere midpoint is situated in the specimen holder 14, more precisely on the axis of rotation. In this way, the reflector 390 reflects back (in both cases) the scattered radiation 64 captured in the solid angle of the reflector 390 to its origin. In this way, up to twice as many photons of the scattered radiation 64 can be acquired. For an embodiment in which the reflected scattered radiation 64 (in the form of an almost parallel bundle of rays) goes past the specimen vessel 56, reference is made to the exemplary embodiment of the apparatus 510 described below.

Alternatively, for a comparable increase in sensitivity or reduction in intensity of the incident pencil beam 38, instead of a reflector 390 two or more reflector segments may also have been arranged around the specimen holder 14.

All the further features of the third exemplary embodiment correspond to those of the first or second exemplary embodiment. In particular, mutually corresponding assemblies 12, 14, 16 and the components thereof have the same degrees of freedom.

The following processes are capable of being implemented with the apparatus 310 which has been described: FLIM (fluorescence-lifetime imaging microscopy); MPM (multiphoton microscopy); FRET (fluorescence resonance energy transfer); FRAP (fluorescence recovery after photobleaching); STED (stimulated emission depletion), whereby after the pencil beam 38 by way of exciting beam a "tube beam" by way of exclusion beam with substantially cylindrically symmetrical intensity distribution is radiated in; FLIP (fluorescence loss in photobleaching); so-called superresolution microscopy; scattered-light microscopy; possibly the following may also be capable of being implemented: STORM (stochastic optical reconstruction microscopy) and FCS (fluorescence correlation spectroscopy).

Figure 4:
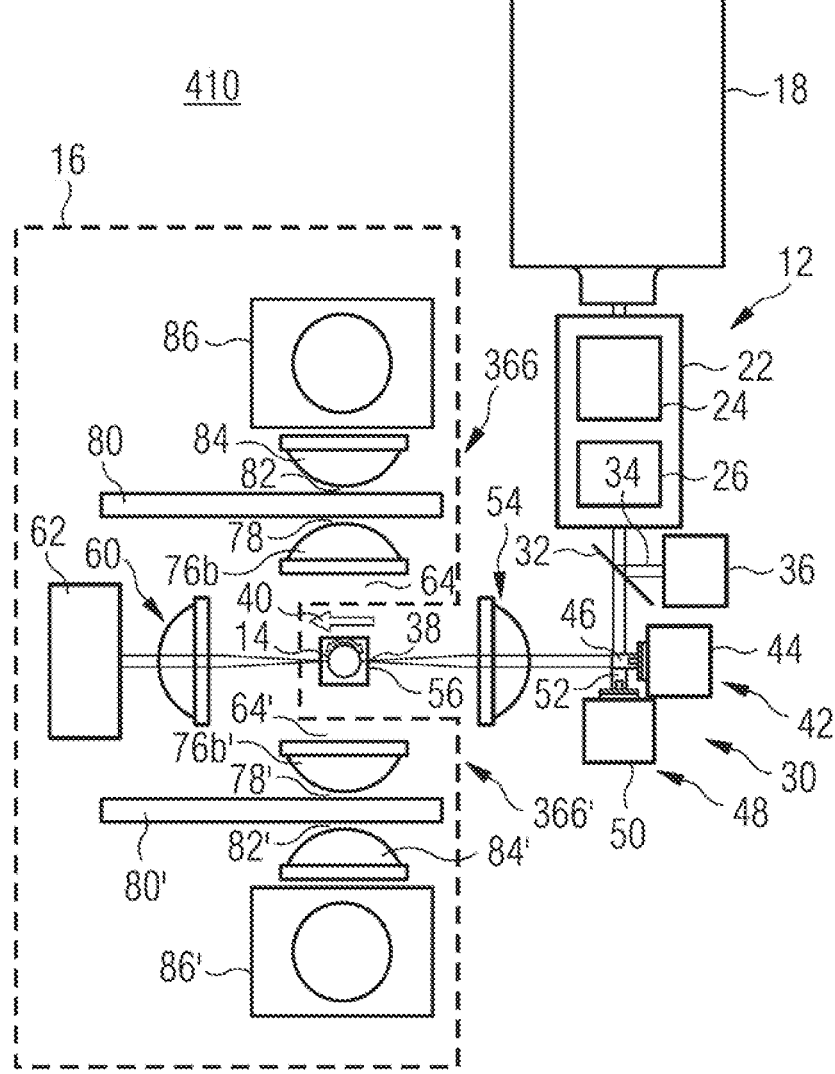

FIG. 4 shows a fourth exemplary embodiment of an apparatus 410 for tomographic image acquisition. For components of the fourth exemplary embodiment having the same reference symbols as in one of the preceding exemplary embodiments, what was described above applies correspondingly, particularly with regard to their properties, constitution, function and their interaction.

The fourth exemplary embodiment differs from one of the preceding exemplary embodiments in that (instead of a scattered-radiation collector 66; 266; 366) two or more scattered-radiation collectors 366, 366' (or, likewise, 66; 266) have been arranged around the specimen holder 14. In other words, the detector unit 16 includes two or more scattered-radiation collectors 366, 366' (or, likewise, 66; 266).

In exemplary embodiments (not shown) with a single signal generator 86, prisms or mirrors have been arranged for the purpose of merging differing beam paths of the collimated scattered radiation 78, 78' of each of the two or more scattered-radiation collectors 366, 366'. The merged collimated scattered radiation is then projected, as described above, onto the single signal generator 86 for the purpose of enlarging an acquired solid angle.

In the exemplary embodiment shown in FIG. 4, a filter-option unit 80; 80', a second collimator 84, 84', and a signal generator 86; 86' have each been assigned to each of the two or more scattered-radiation collectors 366, 366' (or, likewise, 66; 266). In a variant, a common filter option has been synchronised by means of the filter-option units 80, 80', and subsignals of the signal generators 86, 86' are added up into one signal for the purpose of enlarging the acquired solid angle. In an alternative variant, the filter option by means of the filter-option units 80, 80' is independent, and the two or more signals of the signal generators 86, 86' are acquired synchronously. In this way, several signals that correspond to differing colour components in the scattered radiation 64, 64' can be acquired simultaneously. This enables a fast acquisition (and reconstruction) of functionally marked colour images, particularly in the case of fluorescent radiation.

All the further features of the fourth exemplary embodiment correspond to those of the preceding exemplary embodiments In particular, mutually corresponding assemblies 12, 14, 16 and the components thereof have the same degrees of freedom.

The following processes are capable of being implemented with the apparatus 410 which has been described: FLIM (fluorescence-lifetime imaging microscopy); MPM (multiphoton microscopy); FRET (fluorescence resonance energy transfer); FRAP (fluorescence recovery after photobleaching); STED (stimulated emission depletion), whereby after the pencil beam 38 by way of exciting beam a "tube beam" by way of exclusion beam with substantially cylindrically symmetrical intensity distribution is radiated in; FLIP (fluorescence loss in photobleaching); so-called superresolution microscopy; scattered-light microscopy; possibly the following may also be capable of being implemented: STORM (stochastic optical reconstruction microscopy) and FCS (fluorescence correlation spectroscopy).

Figure 5:
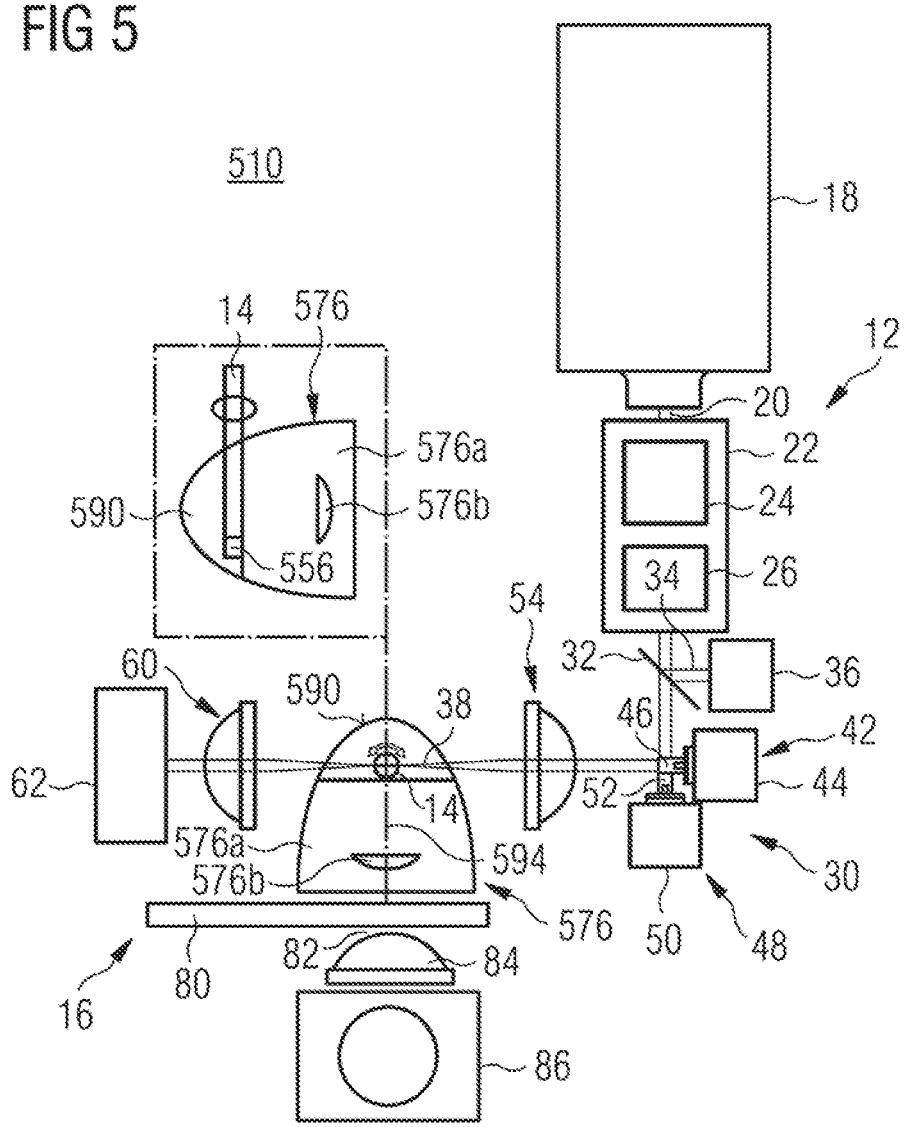

FIG. 5 shows a fifth exemplary embodiment of an apparatus 510 for tomographic image acquisition. For components of the fifth exemplary embodiment having the same reference symbols as in one of the preceding exemplary embodiments, what was described above applies correspondingly, particularly with regard to their properties, constitution, function and their interaction.

The fifth exemplary embodiment differs from one of the preceding exemplary embodiments in that the scattered radiation 64 arises directly in the first collimator 76, particularly in one of its components 76a, 76b. In other words, the first collimator 76 includes (functionally) the specimen vessel 56.

In the exemplary embodiment shown in FIG. 5, a first collimator 576 includes a glass body 576a with (by approximation) the shape of an elongated half ellipsoid of revolution. The first collimator 576 exhibits at its rounded end, over about one third of its axial length, a reflector 590. The reflector 590 can be realised as a reflecting coating on the glass body 576*a*, or includes the plurality of retroreflectors (described in connection with reflector 390).

Still within this third, for instance at one quarter of the axial length, an elongated cuboid collimator recess 556 has been provided. The longitudinal axis of the collimator recess 556 coincides with the (vertical) axis of rotation of the apparatus 510 and intersects the axis of symmetry 594 of the first collimator 576 perpendicularly. The collimator recess 556 extends almost completely over the cross section of the first collimator 576, so that the collimator recess 556 is closed on one side (at the bottom). The collimator recess 556 is dimensioned in such a way that the specimen holder 14 arranged in the collimator recess 556 (over a length enclosing the specimen) is rotatable in non-contacting manner. In this way, the collimator recess 556 acts as the specimen vessel 56 as described above. In particular, the volume between the specimen holder 14 and the collimator recess 556 contains the refractive-index-adapted liquid 58.

To the extent that a non-cuboid collimator recess 556 does not already exhibit plane side surfaces for entrance and exit of the pencil beam 38, appropriate plane windows have been provided in the side surfaces. The pencil beam 38 is focused into the specimen holder by the plane entrance window.

At the end of the first collimator 576 situated opposite the reflector 590, a lens 576*b* has been arranged on the axis of symmetry 594 in a conical recess. The lens 576*b* is designed to be similar to the lens 76*b* described above.

The optical elements 576*a*, 590 and 576*b* have been arranged to direct almost the entire scattered radiation 64 emerging from the specimen holder 14 with slight residual divergence in the direction of the signal generator 86 of the detector unit 16. The scattered radiation reflected back by the reflector 590 into the specimen holder 14 is collimated, together with the directly acquired scattered radiation 64, by the first collimator 576 to such an extent that the acquired radiation can be filtered and detected as described above.

All the further features of the fifth exemplary embodiment correspond to those of the preceding exemplary embodiments. In particular, mutually corresponding assemblies 12, 14, 16 and the components thereof have the same degrees of freedom.

The following processes are capable of being implemented with the apparatus 510 which has been described: FLIM (fluorescence-lifetime imaging microscopy); MPM (multi-photon microscopy); FRET (fluorescence resonance energy transfer); FRAP (fluorescence recovery after photobleaching); STED (stimulated emission depletion), whereby after the pencil beam 38 by way of exciting beam a "tube beam" by way of exclusion beam with substantially cylindrically symmetrical intensity distribution is radiated in; FLIP (fluorescence loss in photobleaching); so-called superresolution microscopy; scattered-light microscopy; possibly the following may also be capable of being implemented: STORM (stochastic optical reconstruction microscopy) and FCS (fluorescence correlation spectroscopy).

In all the exemplary embodiments with only one x-control element 42 a photosensitive surface of the signal generator 86 (in the y-direction) is capable of being made considerably smaller. As described above, this is also possible in the case of variable y-offset by virtue of a synchronous transporting in the y-direction either of the specimen holder 14 and the specimen vessel 56; 256, or of the light-source 12 and the detector unit 16.

Figure 6:
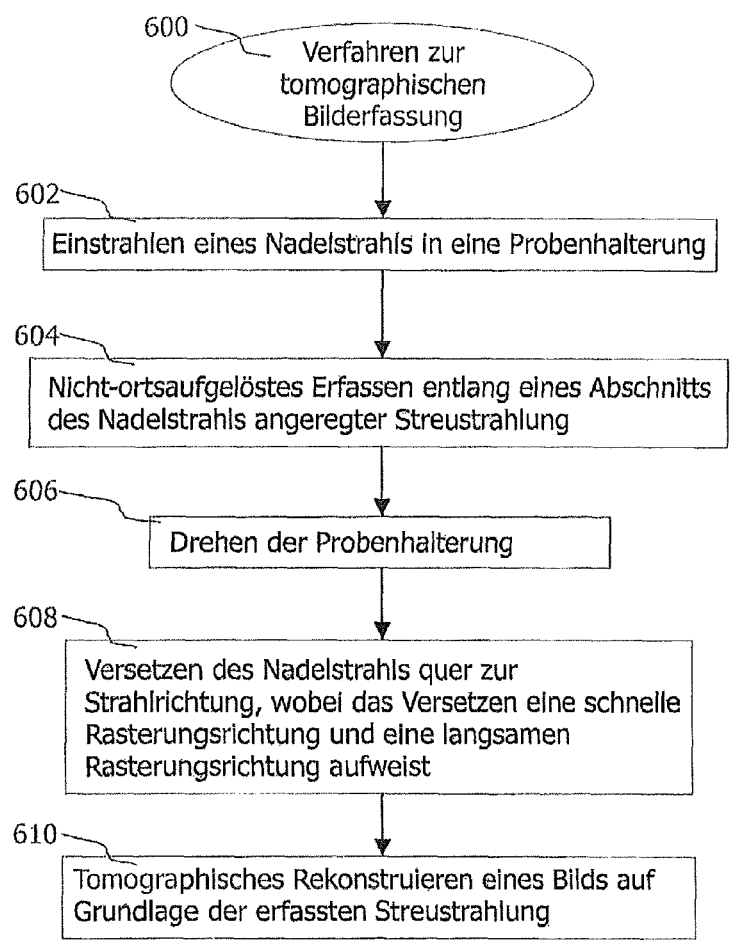

FIG. 6 shows a simplified flow chart of a process 600 for tomographic image acquisition. The process 600 is capable of being implemented by means of any of the exemplary embodiments, described above, of the apparatus 10; 210; 310; 410; 510 for tomographic image acquisition.

The process 600 for tomographic image acquisition comprises the following steps:
  radiating 602 a pencil beam 38 with a beam direction 40 into a (rotatable) specimen holder 14 with a view to the excitation of scattered radiation 64,
  non-spatially-resolved acquiring 604 of the scattered radiation 64 excited along a section of the pencil beam 38,
  substantially parallel offsetting 606 of the pencil beam 38 at right angles to the beam direction 40 of the pencil beam 38 to a plurality of measuring positions with a fast-rasterisation direction and with a slow-rasterisation direction,
  rotating 608 the specimen holder 14 to a plurality of rotary positions for each of the plurality of measuring positions, and
  tomographic reconstructing 610 of an image (in particular, a sectional image or a spatial image) on the basis (of an intensity) of the acquired scattered radiation 64.

The fast-rasterisation direction is preferentially perpendicular to the slow-rasterisation direction. The slow-rasterisation direction may coincide with the axis of rotation. In connection with one of the apparatuses described above, the x-direction may be the fast-rasterisation direction and/or the y-direction may be the slow-rasterisation direction. The offsetting into the measuring positions is also designated as rasterising.

The offsetting can be undertaken by means of the optical control element 30 described above. The pencil beam 38 can be offset in an xy-plane (perpendicular to the beam direction 40) in accordance with a "meandering" contour. Alternatively, the offsetting may exhibit a spiral course or may be undertaken along concentric circles.

The slow-rasterisation direction and the rotation are interchangeable in the process 600. That is to say, (at least) the motion of the slow-rasterisation direction and the rotating commute. This may enable a minimisation of the total acquisition time.

To the extent that the axis of rotation is parallel to the y-direction, the reconstruction can begin already prior to conclusion of a complete image acquisition. Advantageously, after a partial acquisition with respect to the fast-rasterisation direction and with respect to the rotation (i.e. when the rotation occurs "before" the slow-rasterisation direction) has been concluded, an intersecting plane (perpendicular to the slow-rasterisation direction) is reconstructed. In this way, after each complete rotation a partial reconstruction can begin.

A control process (for acquiring the scattered radiation 64) may comprise the offsetting in the fast-rasterisation direction by way of "innermost iteration loop", the rotating by way of "middle iteration loop", and the offsetting in the slow-rasterisation direction by way of "outer iteration loop". The partial reconstruction can begin after conclusion of each "middle iteration loop". Each partial reconstruction is capable of being put into effect independently of a further partial acquisition and independently of a further partial reconstruction. In this way, the partial reconstructions can be effectively parallelised.

As has become evident from the description of various exemplary embodiments, the apparatus 10; 210; 310; 410; 510 and the process 600 enable a tomographic image acquisition of an at least partly transparent specimen which has been suspended in a refractive-index-matching substance. The radiation-source 18 may also include several lasers, the partial raw beams of which have been superimposed on the raw beam 20. In this way, a spectrum of the pencil beam 38 can be realised that has been adapted to several transitions of the fluorophores introduced into the specimen (i.e. several colours)

The technique that has been described can, depending on the exemplary embodiment, offer one or more of the following advantages: ring artefacts, which may arise in the course of optical projection tomography (OPT), are avoided. The sensitivity in respect of fluorescence (in the case of specimens having a dimension of more than one millimeter) is significantly greater than with known techniques. Consequently, a higher specimen throughput is possible, and there is less potential for damage to the specimen. The apparatus 10; 210; 310; 410; 510 requires only components that are available at reasonable cost.

LIST OF REFERENCE SYMBOLS (The last two numerals denote the functional feature. In the case of three-digit reference symbols, the leading numeral corresponds to the Figure.)
10, 210, 310, 410, 510 apparatus for tomographic image acquisition
12 light-source
14 specimen holder
16 detector unit
18 radiation-source
20 raw beam
22 beam-shaping lens system
24 telescopic lens system
26 diaphragms and phase masks
28 shaped beam
30 optical control element
32 beam-splitter
34 partial beam
36 reference detector
38 pencil beam
40 beam direction
42 x-control element
44 x-actuator
46 x-rasterisation mirror
48 y-control element
50 y-actuator
52 y-rasterisation mirror
54 (first) focusing lens system
56, 256, 556 specimen vessel; collimator recess
58 liquid
59 glass surface
60 second focusing lens system
62 transmission photodetector
64, 64' scattered radiation
66, 266, 366, 366' scattered-radiation collector
68 integrator
69, 269 inner surface, reflecting surface
70, 27 illumination aperture
72, 272 measuring aperture; transparent bottom aperture
74, 274 transmission aperture
76, 576 first collimator
576a glass body
76a, 576a light guide, in partic. optical hollow-core conductor
76b, 576b lens
78' partly collimated scattered radiation
78 collimated scattered radiation
80, 80' filter-option unit
82 filtered scattered radiation
84 second collimator
86, 86' signal generator
88 stepper motor
390, 590 reflector
594 axis of symmetry

The invention claimed is:

1. Apparatus for tomographic image acquisition, comprising
   a specimen holder,
   a light-source which is configured to generate a pencil beam having a beam direction traversing a specimen volume of the specimen holder provided for receiving a specimen, and which exhibits an optical control element that is able to offset the pencil beam traversing the specimen volume of the specimen holder at right angles to the beam direction with unchanged beam direction, and
   a detector unit configured for a non-spatially-resolved acquisition of at least a portion of scattered radiation escaping from a section of the pencil beam within the specimen volume of the specimen holder, wherein the scattered radiation includes radiation scattered out of the beam direction.

2. Apparatus according to claim 1, wherein the pencil beam traverses the specimen holder and/or the specimen.

3. Apparatus according to claim 1, wherein the specimen holder and the light-source are rotatable relative to one another about an axis of rotation.

4. Apparatus according to claim 3, wherein the beam direction is perpendicular to the axis of rotation.

5. Apparatus according to claim 3, wherein the detector unit is stationary.

6. Apparatus according to claim 1, wherein the pencil beam exhibits a beam waist within the specimen volume or the specimen holder having a Rayleigh length that is equal to or greater than half the length of the section of the pencil beam to be acquired by the detector unit.

7. Apparatus according to claim 1, wherein the section of the pencil beam to be acquired by the detector unit encompasses the entire pencil beam traversing the specimen volume or the specimen holder.

8. Apparatus according to claim 1, wherein the scattered radiation is a Raman scattered radiation or fluorescent radiation excited by the pencil beam.

9. Apparatus according to claim 8, wherein the scattered radiation is a Raman scattered radiation of a Stokes-Raman scattering.

10. Apparatus according to claim 1, wherein the light-source is further configured to generate the pencil beam in the visible spectrum, in the ultraviolet spectrum or in the infrared spectrum.

11. Apparatus according to claim 1, wherein the light-source is further configured to generate the pencil beam (38) in intense pulses for multi-photon excitation.

12. Apparatus according to claim 1, wherein the light-source is further configured to generate the pencil beam with a limited bandwidth.

13. Apparatus according to claim 12, wherein the detector unit is further configured to acquire the scattered radiation only at a wavelength or in a wavelength range outside the limited bandwidth.

14. Apparatus according to claim 12, wherein the limited bandwidth is configured to excite one or more selected transitions of a fluorophore in the specimen.

15. Apparatus according to claim 12, wherein the scattered radiation includes fluorescent radiation and the detector unit includes fluorescence filters which are transparent to the fluorescent radiation.

16. Apparatus according to claim 12, wherein the scattered radiation includes fluorescent radiation and the detector unit includes fluorescence filters which are opaque within the bandwidth of the pencil beam.

17. Apparatus according to claim 12, wherein the light-source is further configured to generate the pencil beam by monochromatic laser radiation.

18. Apparatus according to claim 1, wherein the specimen holder is rotatably arranged in a beam-transparent specimen vessel, on which plane surfaces for entrance of the pencil beam into the specimen holder and/or for exit of the pencil beam from the specimen holder are provided, and wherein in the volume between the specimen holder and the specimen vessel a liquid with refractive index adapted to the specimen holder is provided.

19. Apparatus according to claim 1, wherein the detector unit further exhibits a signal generator with a semiconductor detector or with a photomultiplier tube.

20. Apparatus according to claim 19, wherein the scattered-radiation collector includes a first collimator arranged between the specimen volume or the specimen holder and the signal generator.

21. Apparatus according to claim 1, wherein the detector unit exhibits at least one scattered-radiation collector configured to acquire the scattered radiation in a solid angle around the specimen volume or the specimen holder of at least $\pi$ sr or $2\pi$ sr.

22. Apparatus according to claim 1, wherein a first collimator exhibits a collimator recess intersecting the optical axis of said collimator by way of specimen vessel.

23. Apparatus according to claim 22, wherein the first collimator includes a reflector configured for retroreflection of a portion of the scattered radiation into the specimen volume or into the specimen holder.

24. Apparatus according to claim 23, wherein the reflector includes a concave mirror or a plurality of retroreflectors.

25. Process for tomographic image acquisition, comprising:
radiating a pencil beam with a beam direction into a specimen volume of a specimen holder provided for receiving a specimen for the excitation of scattered radiation,
non-spatially-resolved acquiring of the scattered radiation excited along a section of the pencil beam, wherein the scattered radiation includes radiation scattered out of the beam direction,
parallel offsetting of the pencil beam at right angles to the beam direction of the pencil beam into a plurality of measuring positions, the offsetting exhibiting a fast-rasterisation direction and a slow-rasterisation direction,
rotating of the specimen holder into a plurality of rotary positions, and
tomographic reconstructing of an image on the basis of the acquired scattered radiation.

\* \* \* \* \*